United States Patent
Mueller et al.

(10) Patent No.: US 10,451,543 B2
(45) Date of Patent: Oct. 22, 2019

(54) INTEGRATED PHOTO-ACOUSTIC GAS SENSOR MODULE

(71) Applicant: Infineon Technologies AG, Neubiberg (DE)

(72) Inventors: Thomas Mueller, Lappersdorf (DE); Horst Theuss, Wenzenbach (DE); Klaus Elian, Alteglofsheim (DE); Rainer Markus Schaller, Saal a.d. Donau (DE); Stefan Kolb, Unterschleissheim (DE)

(73) Assignee: Infineon Technologies AG, Neubiberg (DE)

( * ) Notice: Subject to any disclaimer, the term of this patent is extended or adjusted under 35 U.S.C. 154(b) by 104 days.

(21) Appl. No.: 15/349,438

(22) Filed: Nov. 11, 2016

(65) Prior Publication Data
US 2017/0212036 A1    Jul. 27, 2017

(30) Foreign Application Priority Data

Jan. 22, 2016 (DE) .................. 10 2016 101 148
Mar. 1, 2016 (DE) .................. 10 2016 103 646

(51) Int. Cl.
*G01N 21/17* (2006.01)
*A61B 5/00* (2006.01)
(Continued)

(52) U.S. Cl.
CPC ....... *G01N 21/1702* (2013.01); *A61B 5/0095* (2013.01); *G01N 29/032* (2013.01);
(Continued)

(58) Field of Classification Search
CPC ....... G01N 2021/1704; G01N 21/1702; G01N 2291/021; G01N 29/032; G01N 29/222;
(Continued)

(56) References Cited

U.S. PATENT DOCUMENTS 5,616,826 A * 4/1997 Pellaux .............. G01N 21/1702
250/343
5,852,308 A * 12/1998 Wood .................. G01N 21/171
257/252

(Continued)

FOREIGN PATENT DOCUMENTS

DE    10 2014 114 672 A1    4/2015
DE    20 2015 002 315 U1    6/2015
DE    10 2015 106 373 A1    10/2016

OTHER PUBLICATIONS

Ishaku, Lucky Ahmed, and David Hutson. "A Resonant Photoacoustic CO 2 Sensor Based on MID-IR LED and MEMS Microphone Technology Operating at 4.3 μM." Abstract. (2016).*

(Continued)

*Primary Examiner* — Jonathan M Dunlap
(74) *Attorney, Agent, or Firm* — Dicke, Billig & Czaja PLLC

(57) ABSTRACT

A photo-acoustic gas sensor is disclosed. The photo-acoustic gas sensor includes a substrate, a light emitter unit supported by the substrate, the light emitter unit including a light emitter configured to emit a beam of light pulses with a predetermined repetition frequency and wavelength corresponding to an absorption band of a gas to be sensed, and a detector unit supported by the substrate, the detector unit including a microphone, wherein the beam of light pulses traverses an area intended to accommodate the gas and the microphone can receive a signal oscillating with the repetition frequency.

22 Claims, 10 Drawing Sheets

(51) Int. Cl.
   *G01N 29/032* (2006.01)
   *G01N 29/22* (2006.01)
   *G01N 29/24* (2006.01)
   *G01N 29/48* (2006.01)
   *G01N 33/00* (2006.01)

(52) U.S. Cl.
   CPC ....... *G01N 29/222* (2013.01); *G01N 29/2418* (2013.01); *G01N 29/48* (2013.01); *G01N 33/0009* (2013.01); *A61B 2562/0204* (2013.01); *G01N 2021/1704* (2013.01); *G01N 2291/021* (2013.01); *H01L 2224/48091* (2013.01); *H01L 2224/48137* (2013.01); *H01L 2224/48247* (2013.01)

(58) Field of Classification Search
   CPC ............... G01N 29/2418; G01N 29/48; G01N 33/0004; H01L 2224/48137; A61B 2562/0204; A61B 5/0095
   See application file for complete search history.

(56) References Cited

U.S. PATENT DOCUMENTS

| | | | | |
|---|---|---|---|---|
| 5,869,749 | A * | 2/1999 | Bonne | G01N 21/03 250/339.12 |
| 5,886,249 | A * | 3/1999 | Bonne | G01N 21/03 250/339.12 |
| 5,933,245 | A * | 8/1999 | Wood | G01N 21/1702 356/246 |
| 6,006,585 | A * | 12/1999 | Forster | G01N 21/1702 250/343 |
| 6,082,178 | A * | 7/2000 | Bernstein | G01N 21/1702 73/24.02 |
| 6,344,647 | B1 * | 2/2002 | Jourdain | G01N 21/1702 250/339.07 |
| 8,359,904 | B2 * | 1/2013 | Nicoletti | B82Y 15/00 356/437 |
| 8,695,402 | B2 * | 4/2014 | Thorson | G01N 21/1702 73/24.02 |
| 9,192,306 | B2 * | 11/2015 | Chen | A61B 5/0086 |
| 9,243,998 | B2 * | 1/2016 | Avramescu | G01N 21/1702 |
| 9,513,261 | B2 * | 12/2016 | Dehe | G01N 29/2418 |
| 9,958,381 | B2 * | 5/2018 | Sakai | G01N 21/3504 |
| 10,018,556 | B2 * | 7/2018 | Sakai | G01N 21/3504 |
| 2002/0017617 | A1 * | 2/2002 | Schuth | B01J 19/0046 250/492.1 |
| 2002/0194897 | A1 * | 12/2002 | Arnott | G01N 21/1702 73/23.31 |
| 2003/0090663 | A1 * | 5/2003 | Autrey | G01N 21/1702 356/432 |
| 2005/0054907 | A1 * | 3/2005 | Page | A61B 5/0095 600/316 |
| 2010/0268058 | A1 * | 10/2010 | Chen | A61B 5/0086 600/407 |
| 2010/0317939 | A1 * | 12/2010 | Kuhn | A61B 5/0084 600/323 |
| 2011/0094291 | A1 * | 4/2011 | Gidon | G01N 21/1702 73/24.02 |
| 2011/0296900 | A1 * | 12/2011 | Thorson | G01N 21/1702 73/24.02 |
| 2012/0151995 | A1 * | 6/2012 | Schade | G01N 21/1702 73/24.02 |
| 2013/0086977 | A1 * | 4/2013 | Wong | G01J 5/045 73/31.05 |
| 2013/0174645 | A1 * | 7/2013 | Willett | G01N 21/1702 73/30.04 |
| 2013/0239658 | A1 * | 9/2013 | Lust | G01N 21/17 73/24.02 |
| 2015/0101395 | A1 | 4/2015 | Dehe et al. | |
| 2015/0377775 | A1 * | 12/2015 | Sakai | G01N 21/3504 250/338.1 |
| 2016/0282259 | A1 | 9/2016 | Kolb et al. | |
| 2016/0313288 | A1 * | 10/2016 | Theuss | G01N 29/2425 |
| 2017/0205340 | A1 * | 7/2017 | Sakai | G01N 21/3504 |
| 2018/0003679 | A1 * | 1/2018 | Prinzhorn | G01B 17/025 |

OTHER PUBLICATIONS

Firebaugh, Samara L., Klavs F. Jensen, and Martin A. Schmidt. "Miniaturization and integration of photoacoustic detection with a microfabricated chemical reactor system." Journal of microelectromechanical Systems 10.2 (2001): 232-237.*

Heaps, David A., and Paul M. Pellegrino. "Examination of quantum cascade laser source for a MEMS-scale photoacoustic chemical sensor." Chemical and Biological Sensing VII. vol. 6218. International Society for Optics and Photonics, 2006.*

Glière, Alain, et al. "Challenges in the design and fabrication of a lab-on-a-chip photoacoustic gas sensor." Sensors 14.1 (2014): 957-974.*

Nicoletti, S., et al. "Challenges in the realization of a fully integrated optical lab-on-chip." Sensors, 2014 IEEE. IEEE, 2014.*

Glière, A., et al. "A coupled model for the simulation of miniaturized and integrated photoacoustic gas detector." International Journal of Thermophysics 34.11 (2013): 2119-2135.*

* cited by examiner

INTEGRATED PHOTO-ACOUSTIC GAS SENSOR MODULE

CROSS-REFERENCE TO RELATED APPLICATION

This Utility patent application claims priority to German Patent Application No. 10 2016 101 148.7, filed Jan. 22, 2016 and German Patent Application No. 10 2016 103 646.3, filed Mar. 1, 2016; both of which are incorporated herein by reference.

FIELD

The present disclosure relates to a photo-acoustic gas sensor, to a photo-acoustic gas sensor module, and to a method for fabricating a photo-acoustic gas sensor.

BACKGROUND

In the past many types of gas detection devices have been developed in order to detect that the atmosphere or the environment contains potentially harmful or hazardous components and, if possible, to provide a warning thereof to a person. The proper function of gas detectors can be of great importance in many applications, especially when these detectors are used for insuring the safety of working personal. Besides that, the space consumption of gas detectors also becomes more and more important as the size of many apparatuses and instruments are continuously getting smaller. This overall trend of miniaturization creates a need to develop more compact gas sensors which can be easily incorporated into existing apparatuses or instruments.

SUMMARY

In accordance with a first aspect of the disclosure a photo-acoustic gas sensor includes a substrate, a light emitter unit supported by the substrate, the light emitter unit including a light emitter configured to emit a beam of light pulses with a predetermined repetition frequency and wavelength corresponding to an absorption band of a gas to be sensed, and a detector unit supported by the substrate, the detector unit including a microphone, wherein the beam of light pulses traverses an area intended to accommodate the gas and the microphone can receive a signal oscillating with the repetition frequency.

In accordance with a second aspect of the disclosure a photo-acoustic gas sensor module includes a substrate, a light emitter configured to emit a beam of light pulses to be absorbed by a gas, and a detector configured to receive a signal oscillating with a repetition frequency of the light pulses, wherein the light emitter and the detector are supported by the substrate.

In accordance with a third aspect of the disclosure a method for fabricating a photo-acoustic gas sensor includes providing a substrate, fabricating a multiple sensor panel by forming a plurality of gas sensor units, each one of the plurality of gas sensor units being supported by the substrate and including a light emitter unit and a detector unit, and singulating the multiple sensor panel to obtain a plurality of photo-acoustic gas sensors.

In accordance with a forth aspect of the disclosure a photoacoustic gas sensor includes a light emitter unit including a light emitter cavity and a light emitter element disposed in the light emitter cavity, the light emitter element being configured to emit a beam of light pulses with a predetermined repetition frequency and a predetermined wavelength corresponding to an absorption band of a gas to be sensed, and a detector unit including a detector cavity and a detector element disposed in the detector cavity, wherein the beam of light pulses traverses an area intended to accommodate the gas and the detector element is arranged to detect a signal oscillating with the repetition frequency.

In accordance with a fifth aspect of the disclosure a method for fabricating a photoacoustic gas sensor includes providing a light emitter unit including a light emitter cavity and a light emitter element disposed in the light emitter cavity, the light emitter element being configured to emit a beam of light pulses with a predetermined repetition frequency and a predetermined wavelength corresponding to an absorption band of a gas to be sensed, and providing a detector unit including a detector cavity and a detector element disposed in the detector cavity, wherein the beam of light pulses traverses an area intended to accommodate the gas and the detector element is arranged to detect a signal oscillating with the repetition frequency.

BRIEF DESCRIPTION OF THE DRAWINGS

The accompanying drawings are included to provide a further understanding of examples and are incorporated in and constitute a part of this specification. The drawings illustrate examples and together with the description serve to explain principles of the examples. Other examples and many of the intended advantages of examples will be readily appreciated as they become better understood by reference to the following detailed description. The elements of the drawings are not necessarily to scale relative to each other. Like reference numerals designate corresponding similar parts.

DETAILED DESCRIPTION

Figure 1:
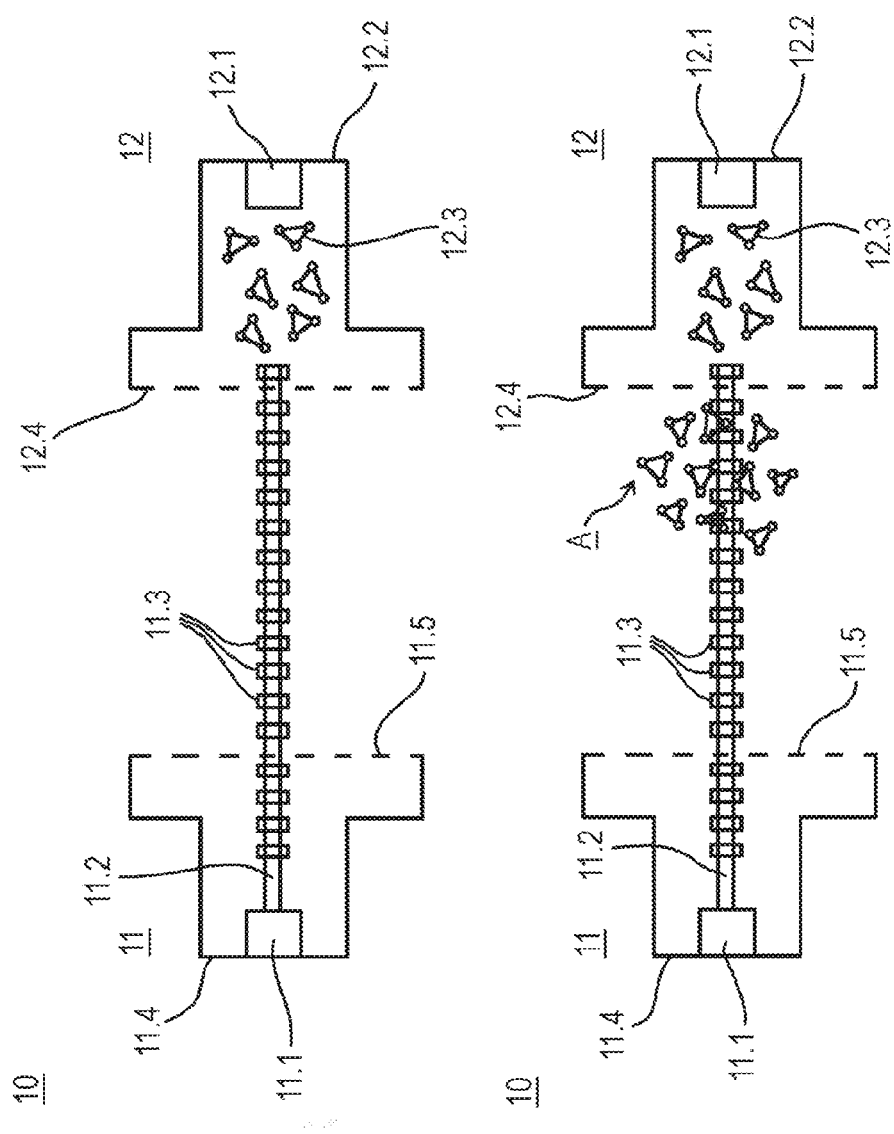
FIG. 1 includes FIGS. 1A and 1B and shows a photo-acoustic gas sensor according to an example, also indicating the measurement principle.

The aspects and examples are now described with reference to the drawings, wherein like reference numerals are generally utilized to refer to like elements throughout. In the following description, for purposes of explanation, numerous specific details are set forth in order to provide a thorough understanding of one or more aspects of the examples. It may be evident, however, to one skilled in the art that one or more aspects of the examples may be practiced with a lesser degree of the specific details. In other instances, known structures and elements are shown in schematic form in order to facilitate describing one or more aspects of the examples. It is to be understood that other examples may be utilized and structural or logical changes may be made without departing from the scope of the present disclosure. It should be noted further that the drawings are not to scale or not necessarily to scale.

In the following detailed description, reference is made to the accompanying drawings, which form a part hereof, and in which is shown by way of illustration specific aspects in which the examples of the disclosure may be practiced. In this regard, directional terminology, such as "top", "bottom", "front", "back", etc., may be used with reference to the orientation of the figures being described. Since components of described devices may be positioned in a number of different orientations, the directional terminology may be used for purposes of illustration and is in no way limiting. It is understood that other aspects may be utilized and structural or logical changes may be made without departing from the scope of the present disclosure. The following detailed description, therefore, is not to be taken in a limiting sense, and the scope of the present disclosure is defined by the appended claims.

It is to be understood that the features of the various examples described herein may be combined with each other, unless specifically noted otherwise.

As employed in this specification, the terms "bonded", "attached", "connected", "coupled" and/or "electrically connected/electrically coupled" are not meant to mean that the elements or layers must directly be contacted together; intervening elements or layers may be provided between the "bonded", "attached", "connected", "coupled" and/or "electrically connected/electrically coupled" elements, respectively. However, in accordance with the disclosure, the above-mentioned terms may, optionally, also have the specific meaning that the elements or layers are directly contacted together, i.e. that no intervening elements or layers are provided between the "bonded", "attached", "connected", "coupled" and/or "electrically connected/electrically coupled" elements, respectively.

Further, the word "over" used with regard to a part, element or material layer formed or located "over" a surface may be used herein to mean that the part, element or material layer be located (e.g. placed, formed, deposited, etc.) "indirectly on" the implied surface with one or more additional parts, elements or layers being arranged between the implied surface and the part, element or material layer. However, the word "over" used with regard to a part, element or material layer formed or located "over" a surface may, optionally, also have the specific meaning that the part, element or material layer be located (e.g. placed, formed, deposited, etc.) "directly on", e.g. in direct contact with, the implied surface.

In addition, while a particular feature or aspect of an example may be disclosed with respect to only one of several implementations, such feature or aspect may be combined with one or more other features or aspects of the other implementations as may be desired and advantageous for any given or particular application. Furthermore, to the extent that the terms "include", "have", "with" or other variants thereof are used in either the detailed description or the claims, such terms are intended to be inclusive in a manner similar to the term "comprise". The terms "coupled" and "connected", along with derivatives may be used. It should be understood that these terms may be used to indicate that two elements co-operate or interact with each other regardless whether they are in direct physical or electrical contact, or they are not in direct contact with each other. Also, the term "exemplary" is merely meant as an example, rather than the best or optimal. The following detailed description, therefore, is not to be taken in a limiting sense, and the scope of the present disclosure is defined by the appended claims.

The examples of detector modules described herein may include microphone chips. The microphone chips may be semiconductor chips. The semiconductor chips can be manufactured on the basis of a specific semiconductor material, for example Si, SiC, SiGe, GaAs, GaN, AlGaAs, but can also manufactured on the basis of any other semiconductor material and, furthermore, may contain inorganic and/or organic materials that are not semiconductors, such as for example insulators, plastics or metals. The microphone chips can be fabricated by MEMS (micro-opto electro-mechanical) technology.

The examples of a photo-acoustic gas sensor may include an encapsulant or encapsulating material having one or more of the chips embedded therein. The encapsulating material can be any electrically insulating material like, for example, any kind of molding material, any kind of resin material, or any kind of epoxy material. The encapsulating material can also be a polymer material, a polyimide material, a thermoplast material, a silicone material, a ceramic material, and a glass material. The encapsulating material may also include any of the above-mentioned materials and further include filler materials embedded therein like, for example, thermally conductive increments. These filler increments can be made of AlO or $Al_2O_3$, AlN, BN, or SiN, for example. Furthermore the filler increments may have the shape of fibers and can be made of carbon fibers or nanotubes, for example.

Insofar as methods for fabricating a photoacoustic gas sensor are described as having a specific order of method steps, it should be mentioned that any other appropriate order of the method steps may be employed by the skilled person. It should further be mentioned that any comments, remarks or features mentioned in connection with a described method are to be understood as also disclosing a device being obtained or resulting from such comments, remarks or features, even if such a device is not explicitly described or illustrated in the figures. Furthermore any comments, remarks or features mentioned in connection with a device are to be understood as also disclosing a method step for providing or fabricating the respective device feature.

FIG. 1 includes FIGS. 1A and 1B and shows an example of a photo-acoustic gas sensor in the left-sided diagrams which together with the right-sided diagrams illustrate the working principle of the photo-acoustic gas sensor. The photo-acoustic gas sensor 10 of FIG. 1 includes a light emitter unit 11 including a light emitter 11.1 configured to emit a beam 11.2 of light pulses 11.3 with a predetermined repetition frequency and a wavelength corresponding to an absorption band of a gas to be sensed. The photo-acoustic gas sensor 10 further includes a detector unit 12 including a microphone 12.1. The light emitter unit 11 is arranged so that the beam 11.2 of light pulses 11.3 traverses an area A configured to accommodate the gas and the detector unit 12 is arranged so that the microphone 12.1 can receive a signal oscillating with the repetition frequency. The reference signs 12.2, 12.3 and 12.4 designate a detector module housing, a reference gas, and a light inlet window, respectively, which are optional elements of the photo-acoustic sensor 10 of FIG. 1.

The light pulses modulated with the repetition frequency will be absorbed by the gas and generate a local pressure pulse which produces a characteristic signal in the microphone. The absorption is specific for the gas, in particular it corresponds to a specific transition in its characteristic rotation-vibration spectrum, so that, by applying appropriate excitation frequencies, a selective photo-acoustic gas sensor can be built. A particular challenge is to construct a compact, miniaturized photo-acoustic gas sensor which can easily be handled, transported or mounted on different sorts of substrates.

According to an example of the photo-acoustic gas sensor 10 of FIG. 1, the detector unit 12 includes a detector unit housing 12.2, wherein the microphone 12.1 is disposed in the detector unit housing 12.2 and a reference gas, indicated by reference sign 12.3, is enclosed in the detector unit housing 12.2, the reference gas 12.3 being of the same species as the gas to be sensed wherein the latter is provided in the area A. According to a further example thereof, the reference gas 12.3 is hermetically sealed in the detector unit housing 12.2 and the detector unit housing 12.2 includes at a side facing the emitter module a light entrance window 12.4 which is transmissive for light emitted by the light emitter 11.1. The gas 12.3 being hermetically sealed in the housing 12.2 can thus be designated as a reference gas or the inner volume of the detector unit housing 12.2 can be designated as a reference volume. The gas to be sensed is disposed in the area A, in particular within a light path between the emitter module 11 and the detector module 12. The measurement principle is thus configured in such a way that in a case where no gas is present to be sensed in the area A, in particular in the light path between the emitter module 11 and the light entrance window 12.4 of the detector module 12, the light pulses enter into the reference volume without any attenuation so that the signal measured and delivered by the microphone 12.1 will be maximum as can be seen in the time diagram of FIG. 1A. On the other hand, if there is gas present to be sensed in the area A, in particular in the light path between the emitter module 11 and the light entrance window 12.4 of the detector module 12, the light pulses will be attenuated so that light pulses of less intensity will enter the reference volume resulting in a decrease of the signal measured and delivered by the microphone 12.1 as indicated in the time diagram of FIG. 1B. Hence in the measurement variant illustrated in FIG. 1 the signal oscillating with the repetition frequency and detected by the microphone emanates from the reference gas. The presence of a gas in area A is indicated by a decrease of the signal strength detected by the microphone 12.1.

According to another example of the photo-acoustic gas sensor, there is no reference gas enclosed in a detector module housing and instead there is only the gas to be sensed present in the area A, in particular in a light path between the emitter module and the microphone. In this case the microphone will not detect and output any signal if no gas to be sensed is present in the light path between the emitter module and the detector module. On the other hand, if gas to be sensed is present in the area A, in particular in the light path between the emitter module and the detector module, the microphone will detect and output a signal the strength of which depends on the amount or density of gas present in area A. Hence in this alternative measurement variant the signal oscillating with the repetition frequency and detected by the microphone emanates from the gas itself. The presence of a gas in area A is indicated by an increase of the signal strength detected by the microphone 12.1. Consequently in this alternative variant a positive signal will be obtained in case of the presence of a gas to be sensed.

According to an example of the photo-acoustic gas sensor 10 of FIG. 1, the repetition frequency of the light pulses lies within an audio frequency range or within a frequency range from 1 Hz to 10 kHz, in particular from 1 Hz to 1 kHz, wherein a typical frequency range is from 1 Hz to 100 Hz corresponding to a pulse duration range from 0.01 s to 1 s.

According to an example of the photo-acoustic gas sensor 10 of FIG. 1, the light emitted by the light emitter 11.1 may include any desired wavelength or wavelength range in the visible or non-visible spectrum. In particular, the light emitter unit 11 is configured to emit only light of a pre-selected wavelength corresponding to the absorption band of the gas to be sensed.

According to an example of the photo-acoustic gas sensor 10 of FIG. 1, the light emitter 11.1 includes one or more of a broad-band emitter, a narrow-band emitter, a coherent light emitter, a non-coherent light emitter, a blackbody radiator, a lamp, a heated resistor, a light emitting diode (LED), or a laser, in particular laser diode. According to an example thereof, in case that the light emitter 11.1 includes a broadband emitter, the light emitter unit 11 may include an optical filter disposed in front of the light emitter 11.1, the optical filter being configured to allow to pass through light of a pre-selected wavelength of the light emitted by the light emitter 11.1. If the light emitter module 11 includes a light emitter module housing 11.4 and a light outlet window 11.5 disposed in a wall of the light emitter unit housing 11.4, the optical filter can be applied onto the light outlet window 11.5 or it can even be identical with the light outlet window 11.5.

According to an embodiment of the photo-acoustic gas sensor 10 of FIG. 1, the light emitter unit 11 includes a tunable wavelength emission range. The tuning of the wavelength of the emitted light pulses depends on the sort of light emitter 11.1 employed. If, for example, the light emitter 11.1 is a narrow-band light source like a light emitting diode (LED) or a laser diode, the tuning of the emission wavelength can be accomplished by directly controlling the light emitter 11.1. If, however, the light emitter 11.1 is a broadband light emitter, the emitted light pulses are filtered by an optical filter, a wavelength tunable optical filter like, e.g. a Fabry-Perot filter, could be employed so that the transmission band of the optical filter could be adjusted by appropriate means. One advantage of a tunable wavelength emission range is that in principle different sorts of gases could be detected.

According to an example of the photo-acoustic gas sensor 10 of FIG. 1, the light emitter unit 11 is configured to emit a beam of light pulses of infrared light of a wavelength corresponding to an energy of a rotational or vibrational band or transition of a molecule of the gas to be sensed.

According to an example of the photo-acoustic gas sensor 10 of FIG. 1, the gas to be sensed is one of $CO_2$, $NO_x$, $H_2O$, $O_2$, $N_2$, $CH_4$ or alcohol.

According to an example of the photo-acoustic gas sensor 10 of FIG. 1, the light emitter unit 11 includes a light emitter unit housing 11.4, wherein the light emitter 11.1 is disposed in the light emitter unit housing 11.4 and the light emitter unit housing 11.4 includes a light outlet window 11.5 in a wall thereof. As already outlined above, the light outlet window 11.5 should have a transmission characteristic which allows to pass through the desired wavelength of the light emitted by the light emitter 11.1. According to a further example thereof, the light outlet window 11.5 could be designed as an optical filter for filtering the desired wavelength or such an optical filter could be attached to the light outlet window 11.5.

According to an example of the photo-acoustic gas sensor 10 of FIG. 1, the light emitter unit 11 and the detector unit 12 are disposed on a common substrate. Specific examples thereof will be shown further below.

According to an example of the photo-acoustic gas sensor 10 of FIG. 1, the light emitter unit 11 and the detector unit 12 are disposed in a face-to-face relationship which means, for example, that a light outlet window 11.5 of the emitter module 11 and a light inlet window 12.4 of the detector module 12 are disposed in a face-to-face relationship as shown in FIG. 1. Further specific examples thereof will be shown further below.

According to an example of the photo-acoustic gas sensor 10 of FIG. 1, the sensor further includes a sensor housing, wherein the light emitter unit and the detector unit are disposed in or attached to the sensor housing. According to a further example thereof, the sensor housing includes a wall having an inner surface which is reflective for light emitted by the light emitter unit. According to a further example thereof, the wall includes an ellipsoidal geometry, wherein the light emitter and the microphone are disposed in the respective focus points of the ellipsoid. Specific examples thereof will be shown further below.

According to a further example, the sensor housing includes a gas inlet opening. According to a further example thereof, the gas inlet opening is covered by a porous foil configured to enable penetration of the gas to be sensed but to prevent penetration of one or more of humidity and particles. Specific examples thereof will be shown further below.

According to an example of the photo-acoustic gas sensor 10 of FIG. 1, the detector module 12 includes one or more further electronic devices like, for example, a logic integrated circuit chip, an ASIC chip, etc. Specific examples thereof will be shown further below.

According to an example of the photo-acoustic gas sensor 10 of FIG. 1, the photo-acoustic gas sensor is configured as a photo-acoustic sensor module which is configured as a surface mount device or a through-hole mount device. Specific examples thereof will be shown further below.

Figure 2:
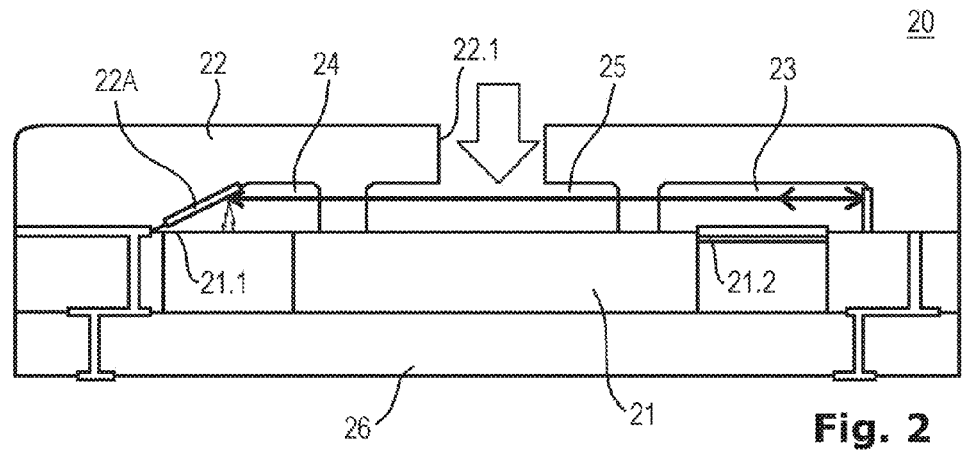
FIG. 2 shows a schematic cross-sectional side view representation of an example of a photo-acoustic gas sensor including a substrate, light emitter and detector integrated in the substrate, a reference volume, a cap member and a bottom member.

FIG. 2 shows an example of a photo-acoustic gas sensor of the first aspect. The photo-acoustic gas sensor 20 of FIG. 2 includes a substrate 21, a light emitter unit supported by the substrate 21, the light emitter unit including a light emitter 21.1 configured to emit a beam of light pulses with a predetermined repetition frequency and wavelength corresponding to an absorption band of a gas to be sensed. The photo-acoustic gas sensor 20 further includes a detector unit supported by the substrate 21, the detector unit including a microphone 21.2. The beam of light pulses traverses an area 25 intended to accommodate the gas and the microphone 21.2 can receive a signal oscillating with the repetition frequency.

According to an example of the photo-acoustic gas sensor 20 of the first aspect, the substrate 21 includes one or more of a semiconductor substrate, a silicon-based substrate, a glass substrate, and a ceramic substrate.

According to an example of the photo-acoustic gas sensor 20 of the first aspect, if the substrate 21 includes a semiconductor substrate, in particular a silicon-based substrate, one or more of the light emitter 21.1 and the microphone 21.2 can be integrated in the semiconductor substrate 21 as it is shown in FIG. 2. According to a further example thereof, the light emitter 21.1 can be formed of a thin film resistor which, in operation, acts as a pulsable infrared emitter. In particular, the thin film resistor can be made of diamond-like nano-structured amorphous carbon and can be pulsed at frequencies up to 70 Hertz with good modulation depth, i.e. contrast between the ON and OFF states. In principle it is also possible that the thin film resistor is made of silicon and is formed contiguous with the semiconductor substrate 21.

According to an example of the photo-acoustic gas sensor 20 of the first aspect, the microphone 21.2 is formed at least in part contiguous with the substrate 21.

According to an example of the photo-acoustic gas sensor of the first aspect, the substrate 21, in particular in case of a semiconductor substrate 21, includes electronic devices or electronic circuitry integrated in the substrate 21. According to a further example thereof, the electronic devices or electronic circuitry can be connected with one or more of the light emitter unit and the detector unit and can perform electrical functions like driving the light emitter unit or processing signals received from the detector unit. Further electrical functions may include signal amplification, signal conditioning, and storing data or calibration information.

According to an example of the photo-acoustic gas sensor of the first aspect, one or more of the light emitter unit and the detector unit includes a prefabricated module attached to the substrate. An example thereof will be shown and explained in more detail below.

According to an example of the photo-acoustic gas sensor of the first aspect, a cap member 22 is disposed above the substrate and is configured to define the area 25 intended to accommodate the gas.

According to an example of the photo-acoustic gas sensor 20 of the first aspect, the cap member 22 includes an opening 22.1 between the environment and the area 25 intended to accommodate the gas.

According to an example of the photo-acoustic gas sensor 20 of the first aspect, the cap member 22 includes one or more of a semiconductor material, a silicon-based material, a glass material, and a ceramic material. In particular the cap member 22 includes a material which is transparent for the beam of light pulses, in particular includes a transmission coefficient for the wavelength of the beam of light pulses which is greater than 50%, more specifically greater than 60%, more specifically greater than 70%, more specifically greater than 80%, more specifically greater than 90%, more specifically greater than 95%, more specifically greater than 98%. In case of a wavelength of 4.3 µm which is appropriate for detecting $CO_2$, silicon can be used as a material for the cap member 22 as silicon is highly transparent for this wavelength. This is of course only relevant if the beam of light pulses has to traverse portions of the cap member which is the case in the example of FIG. 2, but not with other examples of photo-acoustic gas sensors which will be shown and explained later.

According to an example of the photo-acoustic gas sensor 20 of the first aspect, the photo-acoustic gas sensor 20 further includes a reference gas, wherein the detector unit includes a detector unit chamber 23, wherein the substrate 21 and the cap member 22 are further configured to define the detector unit chamber 23 and the reference gas is enclosed in the detector unit chamber 23, wherein the reference gas is of the same species as the gas to be sensed. According to a further example thereof, the detector unit chamber 23 is bounded by a portion of an upper surface of the substrate 21 and one or more surfaces of the cap member 22, wherein the microphone 21.2 is disposed on or integrated in the portion of the upper surface of the substrate 21 as can be seen in FIG. 2.

According to an example of the photo-acoustic gas sensor 20 of the first aspect, the light emitter unit includes a light emitter unit chamber 24, wherein the substrate 21 and the cap member 22 are further configured to define the light emitter unit chamber 24. According to a further example thereof, the light emitter unit chamber 24 is defined by a portion of an upper surface of the substrate 21 and one or more surfaces of the cap member 22 wherein the light emitter 21.1 is disposed on or integrated in the portion of the upper surface of the substrate 21.

According to an example of the photo-acoustic gas sensor 20 of the first aspect, the cap member 22 is configured to deflect the beam of light pulses emitted by the light emitter unit in the direction of an area adjacent to the detector unit. According to a further example thereof, the cap member 22 includes a reflective wall 22A configured to reflect the beam of light pulses emitted by the light emitter 21.1 in the direction of an area adjacent to the microphone 21.2.

According to an example of the photo-acoustic gas sensor 20 of the first aspect, the cap member 22 is connected to the substrate 21 by welding, soldering or anodic bonding processes, or by another bonding process, in particular by a bonding process capable of creating a hermetic bond.

According to an example of the photo-acoustic gas sensor of the first aspect, the photo-acoustic gas sensor includes a bottom member 26 disposed below the substrate 21, wherein the bottom member 26 includes one or more of a semiconductor material, a silicon-based material, a glass material, and a ceramic material.

According to an example of the photo-acoustic gas sensor of the first aspect, the bottom member 26 includes electrical via connections which can be connected with electrical via connections formed in the substrate 21 wherein the substrate via connections and connected with one or more of the light emitter and detector.

According to an example of the photo-acoustic gas sensor 20 of the first aspect, the bottom member 26 is connected to the substrate 21 by welding, soldering or anodic bonding processes, or other bonding processes, in particular bonding processes capable of creating a hermetic bond.

Figure 3:
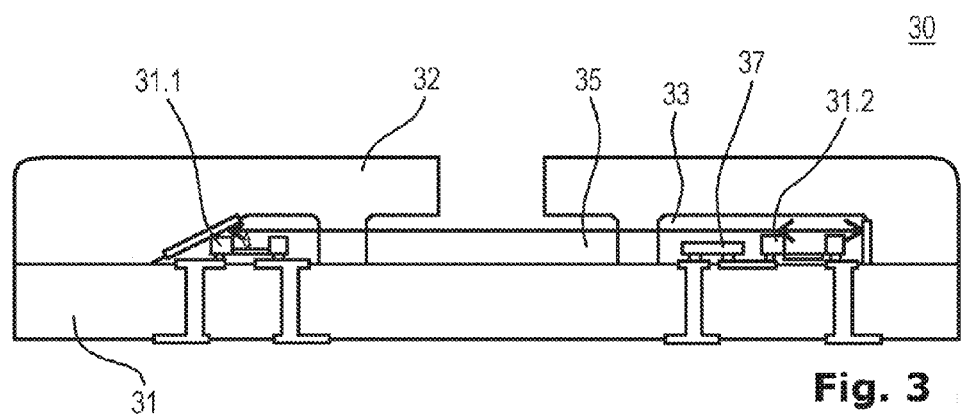
FIG. 3 shows a schematic cross-sectional side view representation of an example of a photo-acoustic gas sensor including a substrate, prefabricated light emitter and detector modules disposed on the substrate, a reference volume and a cap member, wherein the substrate includes electrical via connections.

FIG. 3 shows a schematic cross-sectional side view representation of an example of a photo-acoustic gas sensor of the first aspect. The photo-acoustic gas sensor 30 of FIG. 3 includes a substrate 31, a light emitter unit 31.1 supported by the substrate 31, the light emitter unit 31.1 including a light emitter configured to emit a beam of light pulses with a predetermined repetition frequency and wavelength corresponding to an absorption band of a gas to be sensed. The photo-acoustic gas sensor 30 further includes a detector unit 31.2 supported by the substrate 31, the detector unit 31.2 including a microphone, wherein the beam of light pulses traverses an area 35 intended to accommodate the gas and the microphone can receive a signal oscillating with the repetition frequency.

The photo-acoustic gas sensor 30 of FIG. 3 may be formed similar to the photo-acoustic gas sensor 20 of FIG. 2 with respect to similar parts or features so that the respective descriptions thereof will not be repeated here. Besides that, the photo-acoustic gas sensor 30 of FIG. 3 includes the following differences compared with the photo-acoustic gas sensor 20 of FIG. 2.

In the example of a photo-acoustic gas sensor 30 as shown in FIG. 3, the light emitter unit 31.1 and the detector unit 31.2 are both provided in the form of modules which are prefabricated and attached to the substrate 31. As shown in FIG. 3, this can be accomplished by fabricating the respective modules and connecting them with the substrate 31 by a flip-chip assembly. Alternatively the modules can also be connected with the substrate 31 in the form of an upright chip assembly and by connecting the contact pads of the modules by wire bonds with electrical contact areas formed on the substrate 31.

The photo-acoustic gas sensor 30 of FIG. 3 includes a cap member 32 being disposed above the substrate 31 and being configured to define the area 35 intended to accommodate the gas. The photo-acoustic gas sensor 30 further includes a reference gas and a detector unit chamber 33, wherein the substrate 31 and the cap member 32 are further configured to define the detector unit chamber 33 and the reference gas is enclosed in the detector unit chamber 33, wherein the reference gas is of the same species as the gas to be sensed. In addition to that, a further electronic device 37 is provided within the detector unit chamber 33, wherein the electronic device 37 can also be connected to the substrate 31 in a flip-chip assembly and can be connected with the detector module 31.2 via an electrical contact area provided on the upper surface of the substrate 31. The electronic device 37 can, for example, be one or more of a processor chip, a logic chip, an amplification chip, a signal conditioning chip or a memory chip.

In the example of a photo-acoustic gas sensor 30 of FIG. 3, no bottom member is provided as was the case with the photo-acoustic gas sensor 20 of FIG. 2. In other words, the substrate 31 of the photo-acoustic gas sensor 30 of FIG. 3 fulfills both functions of the substrate 21 and the bottom member 26 of the photo-acoustic gas sensor 20 of FIG. 2.

In the example of a photo-acoustic gas sensor 30 of FIG. 3, the substrate 31 includes electrical via connections connected with electrical contact areas on the upper surface of the substrate 31 and with electrical contact areas on the lower surface of the substrate 31 so that the photo-acoustic gas sensor 30 can be mounted on a substrate in a surface mount technology.

Figure 4:
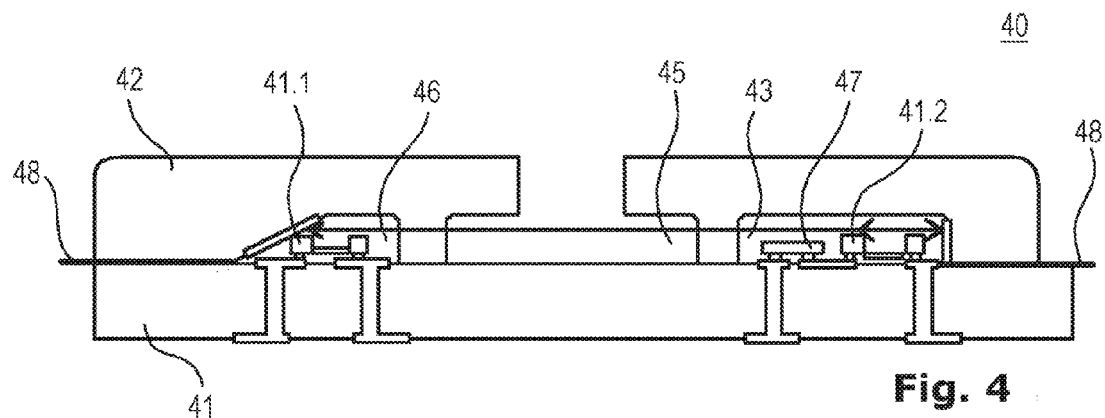
FIG. 4 shows a schematic cross-sectional side view representation of an example of a photo-acoustic gas sensor comparable to the one of FIG. 3, wherein the substrate includes electrical planar connections on an upper surface thereof instead of electrical via connections.

FIG. 4 shows a schematic cross-sectional side view representation of an example of a photo-acoustic gas sensor. The photo-acoustic gas sensor 40 of FIG. 4 differs from the photo-acoustic gas sensor 30 of FIG. 3 in the following aspect. The substrate 41, which may be otherwise comparable with the substrate 31 of FIG. 3, does not include electrical via connections. Instead of electrical via connections the photo-acoustic gas sensor 40 includes electrical contact areas 48 extending from the inside of the detector unit chamber 43 and the inside of the light emitter chamber 46 underneath the cap member 42 to the outside on the upper surface of the substrate 41. The photo-acoustic gas sensor 40 can then be connected to any sort of customer's equipment by an appropriate manner.

Figure 5:
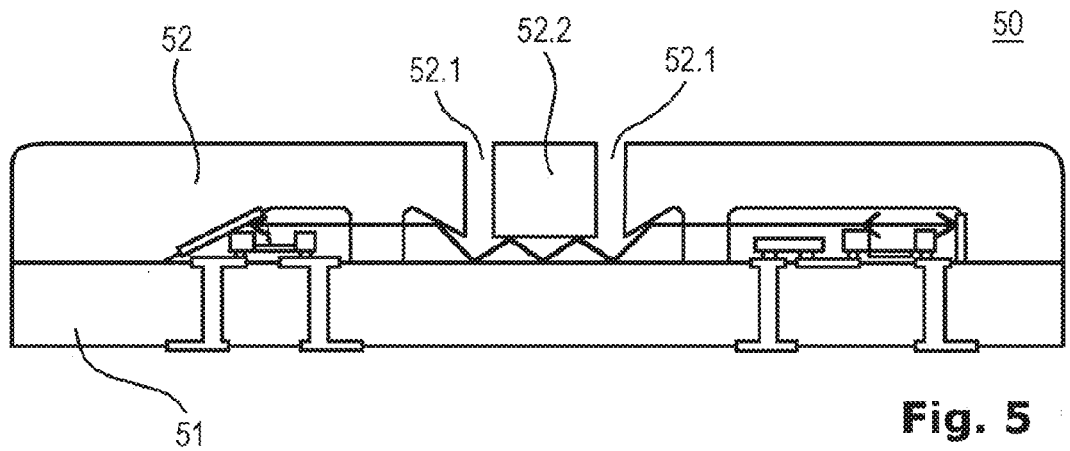
FIG. 5 shows a schematic cross-sectional side view representation of an example of a photo-acoustic gas sensor comparable to the one of FIG. 3, wherein the cap member is configured so as to allow multiple reflections of the beam of light pulses on its path from the light emitter to the detector.

FIG. 5 shows a schematic cross-sectional side view representation of an example of a photo-acoustic gas sensor. The photo-acoustic gas sensor 50 of FIG. 5 is comparable to the ones shown in FIGS. 2 and 3 and differs from these only in the following aspect. The photo-acoustic gas sensors 20 and 30 shown in FIGS. 2 and 3 each include a cap member being provided with a central opening or port for allowing environmental gas to flow into the area intended to accommodate the gas. The photo-acoustic gas sensor 50 of FIG. 5, however, includes a substrate 51 and a cap member 52 disposed above the substrate 51, wherein the cap member 52 includes two or more openings 52.1 arranged, for example, concentrically around a central portion 52.2. The central portion 52.2 includes a lower surface having a reflective coating thereon and also lower surfaces of the cap member 52 on either sides of the central portion 52.2 include respective reflective coatings so that multiple reflections of the beam of light pulses are effected within the area intended to accommodate the gas. This extends the absorption length of the beam of light pulses which has a considerable impact onto the performance and accuracy of the gas sensor. FIG. 5 shows a variant using only reflections in the vertical direction. However, a reflector design with horizontal reflections can be implemented as well.

FIG. 6 includes FIG. 6A-6E and shows schematic cross-sectional side view representations of examples of photo-acoustic gas sensors.

Figure 6A:
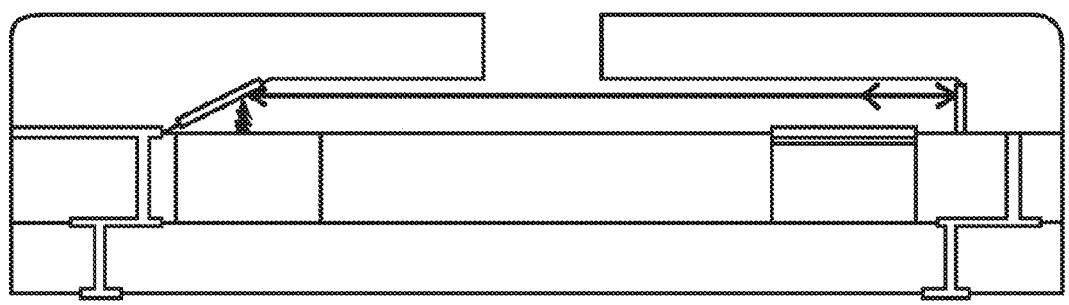
FIG. 6 includes FIG. 6A to 6E and shows schematic cross-sectional side view representations of examples of photo-acoustic gas sensors including an example of a photo-acoustic gas sensor comparable to the one of FIG. 2 by omitting the reference volume (A), an example of a photo-acoustic gas sensor according to the example of (A) with an additional integrated optical filter (B), an example of a photo-acoustic gas sensor comparable to the one of FIG. 3 by omitting the reference volume (C), an example of a photo-acoustic gas sensor comparable to the one of (C) with an additional optical filter (D), and an example of a photo-acoustic gas sensor comparable to the one of (C) with a sealed microphone region (E).

FIG. 6A shows an example of a photo-acoustic gas sensor which is comparable with the example as shown in FIG. 2. The difference to the latter is that the photo-acoustic gas sensor of FIG. 6A includes an "open" microphone with no reference gas chamber. As explained above, in this variant of a photo-acoustic gas sensor a positive signal will be obtained in case of the presence of a gas to be sensed, but the selectivity will be lower as compared to variants provided with a reference gas.

Figure 6B:
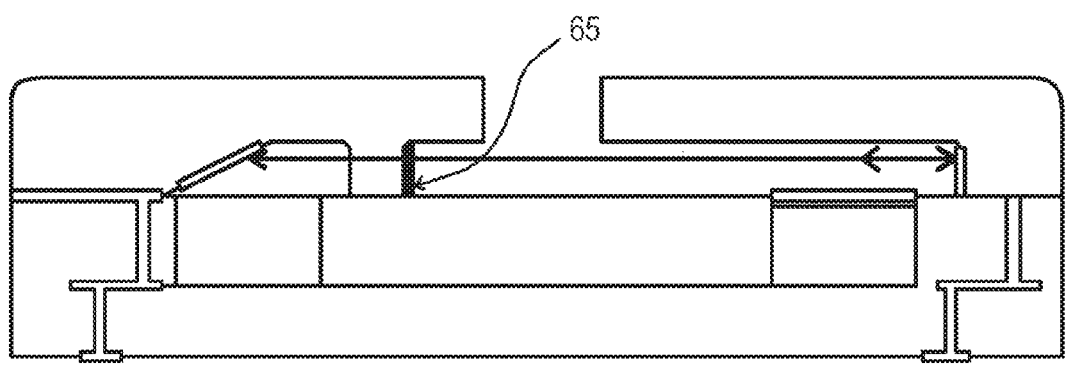

FIG. 6B shows a variant comparable to the one of FIG. 6A, but with an additional integrated optical filter 65 for selective penetration of the desired wavelength. The optical filter 65 provides a wavelength selectivity of the broad band light emitted by the light emitter. The optical filter 65 can be provided by an appropriate coating applied onto an inner wall of the cap member 62.

Figure 6C:
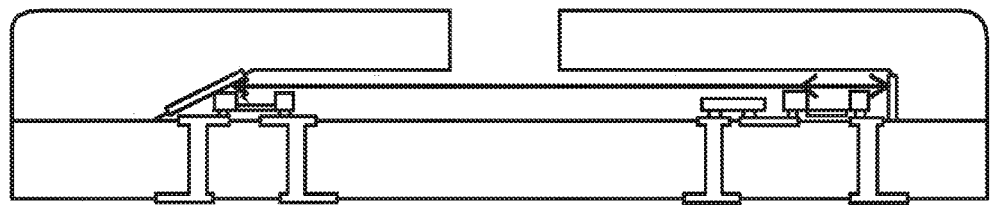

FIG. 6C shows a variant comparable to the one shown in FIG. 3, but again with an "open" microphone and emitter as explained above in connection with FIG. 6A.

Figure 6D:
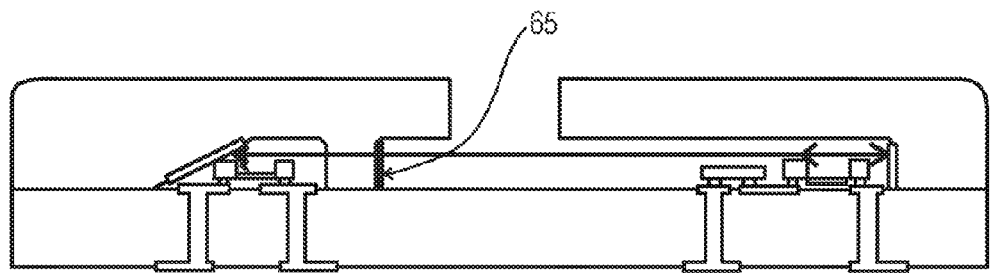

FIG. 6D shows a variant comparable with the one shown and explained above in connection with FIG. 6C wherein, as a difference, an integrated optical filter 65 is provided as shown and explained above in connection with FIG. 6B.

Figure 6E:
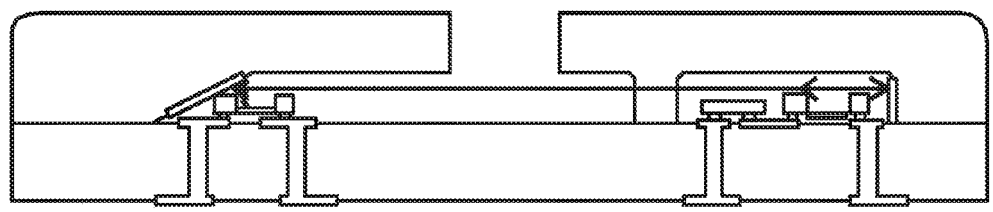

FIG. 6E shows a variant comparable with the one shown and described above in connection with FIG. 6C, wherein the detector unit is sealed from the area intended to accommodate the gas by a wall which is part of the cap member. The detector unit can also be configured as a reference gas chamber and may contain a suitable reference gas. The separating wall of the cap member may also include a coating which acts as an optical filter as described before. The light emitter region can be unsealed or open as shown in FIG. 6E.

The present disclosure also relates to a photo-acoustic gas sensor module according to a second aspect. The photo-acoustic gas sensor according to the second aspect includes a substrate, a light emitter configured to emit a beam of light pulses to be absorbed by a gas, and a detector configured to receive signal oscillating with a repetition frequency of the light pulses, wherein the light emitter and the detector are supported by the substrate.

According to an example of the photo-acoustic gas sensor module of the second aspect, the substrate includes electrical via connections connected with the light emitter and the detector.

According to an example of the photo-acoustic gas sensor module of the second aspect, the photo-acoustic gas sensor further includes a cap member disposed above the substrate, the cap member including a reflective wall configured to reflect the beam of light pulses emitted by the light emitter in the direction of an area adjacent to the detector.

According to an example of the photo-acoustic gas sensor module of the second aspect, the photo-acoustic gas sensor further includes a bottom member disposed below the substrate, the bottom member including electrical via connections.

Further examples of the photo-acoustic gas sensor module of the second aspect can be formed together with anyone of the examples or features described above in connection with the photo-acoustic gas sensor of the first aspect.

The present disclosure also relates to a method for fabricating a photo-acoustic gas sensor according to a third aspect, wherein the method relates to a special form of an extended wafer level (EWL) process for fabricating a plurality of photo-acoustic gas sensors. The method for fabricating a photo-acoustic gas sensor according to the third aspect includes providing a substrate, fabricating a multiple sensor panel by forming a plurality of gas sensor units, each one of the plurality of gas sensor units being supported by the substrate and including a light emitter unit and a detector unit, and singulating the multiple sensor panel to obtain a plurality of photo-acoustic gas sensors.

According to an example of the method of the third aspect, forming the plurality of gas sensor units includes integrating the light emitter unit and the detector unit into an area adjacent to an upper main face of the substrate.

According to an example of the method of the third aspect, forming the plurality of gas sensor units includes prefabricating a light emitter unit and a detector unit and disposing the light emitter unit and the detector unit above an upper main face of the substrate.

Further examples of the method of the third aspect can be formed together with anyone of the examples and features described above in connection with a photo-acoustic gas sensor of the first aspect or a photo-acoustic gas sensor module of the second aspect.

Figure 7A:
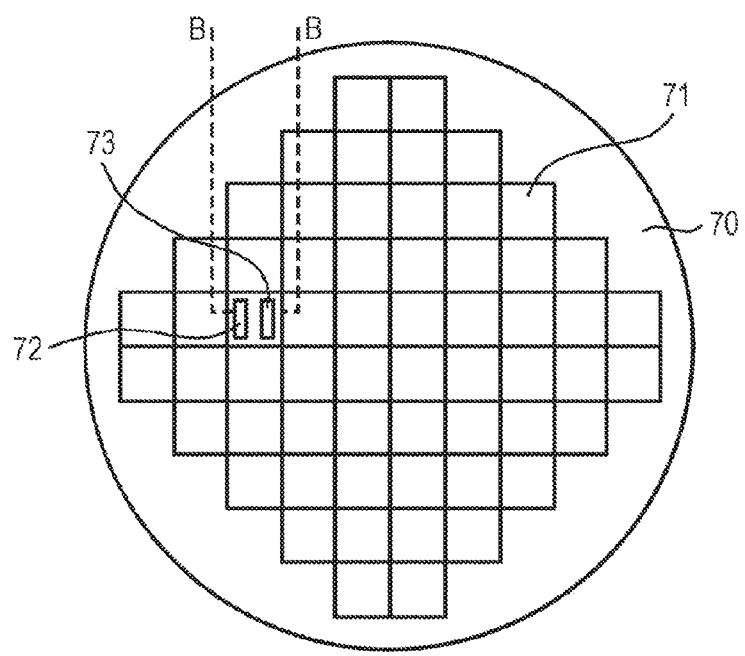
FIG. 7 includes FIGS. 7A and 7B and shows a schematic top view representation of a substrate wafer including a plurality of gas sensor units supported by the substrate wafer (A) and a schematic cross-sectional side view representation along a plane as indicated by line B-B in FIG. 7A illustrating the attachment of a cap member to the substrate wafer for fabricating a plurality of photo-acoustic gas sensors according to FIG. 2 (B).
Figure 7B:
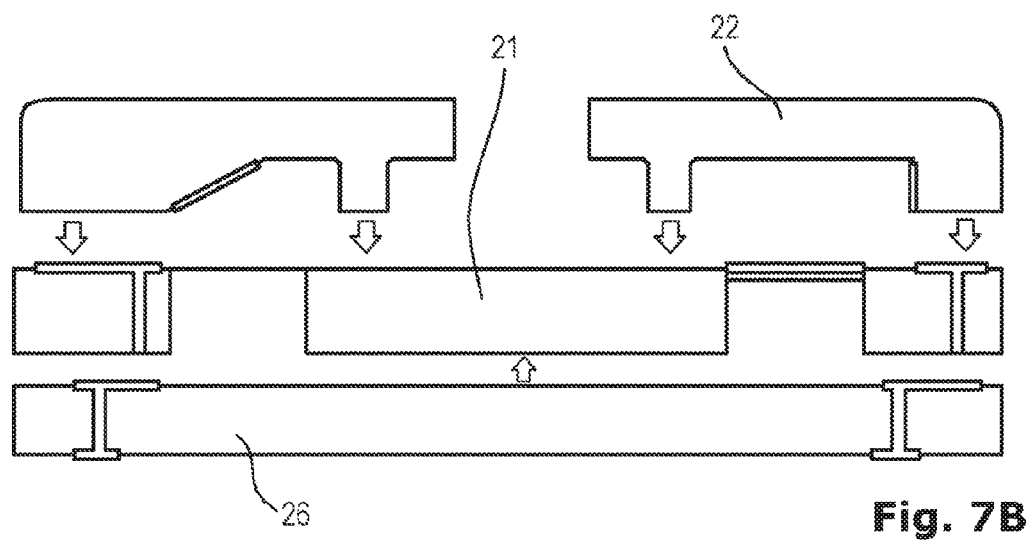

FIG. 7 includes FIGS. 7A and 7B and further illustrates an example of a method according to the third aspect.

FIG. 7A shows a top view representation of an intermediate product of the fabrication process. The intermediate product includes a semiconductor wafer, in particular a silicon wafer 70, as a substrate. The semiconductor wafer 70 contains a plurality of regions 71 which are intended to become respective gas sensor units. The further processing of the semiconductor wafer 70 depends on which one of the examples, as shown in FIGS. 2-6, is intended to be realized. It can be the case, for example, that in one of the first steps electrical via connections can be formed into the silicon wafer 70 in each one of the regions 71. Then electrical contact areas connected with the electrical via connections can be formed on the upper and lower surfaces of the silicon wafer 70 in each one of the regions 71, the electrical contact areas intended to be connected with the light emitters and detectors, respectively. In case that an example such as that of FIG. 2 is to be fabricated, electronic devices and/or electronic circuitry can then be processed in an active upper surface of the silicon wafer 70 in each one of the regions 71, wherein the electronic devices and electronic circuitry are to be intended to be connected with either one or both of the light emitter or the detector. Furthermore, in case that an example such as that of FIG. 2 is to be fabricated, for integrating the light emitter and the detector into the silicon wafer 70, it may be necessary to form empty spaces below the light emitter and the microphone by removing the silicon material from the lower surface of the silicon wafer 70 almost until the upper surface of the silicon wafer 70. Otherwise, if an example such as that shown in FIGS. 3 and 4 is to be fabricated, prefabricated light emitter and detector modules will be connected with the upper surface of the silicon wafer 70 and electrically connected with respective electrical contact areas thereupon.

In any case in each one of the regions 71 of the semiconductor wafer 70, a light emitter unit 72 and a detector unit 73 will be provided.

FIG. 7B shows the next steps of the fabrication process of a photo-acoustic gas sensor according to the example of FIG. 2, i.e. attaching the cap member 22 to the substrate 21 from above and attaching the bottom member 26 to the substrate 21 from below. Both the cap member 22 and the bottom member 26 may have the same shape as the substrate 21, i.e. the silicon wafer 21. Both attaching processes can be performed by one or more of welding, soldering or anodic bonding processes, or by any other connection process capable creating a hermetic bond. It should be added that the fabrication process is not limited to the classical, i.e. circular wafer shapes. It is in principle also possible to use other like quadratic or rectangular shapes of the substrate 21, the cap member 22 and the bottom member 26.

Figure 8:
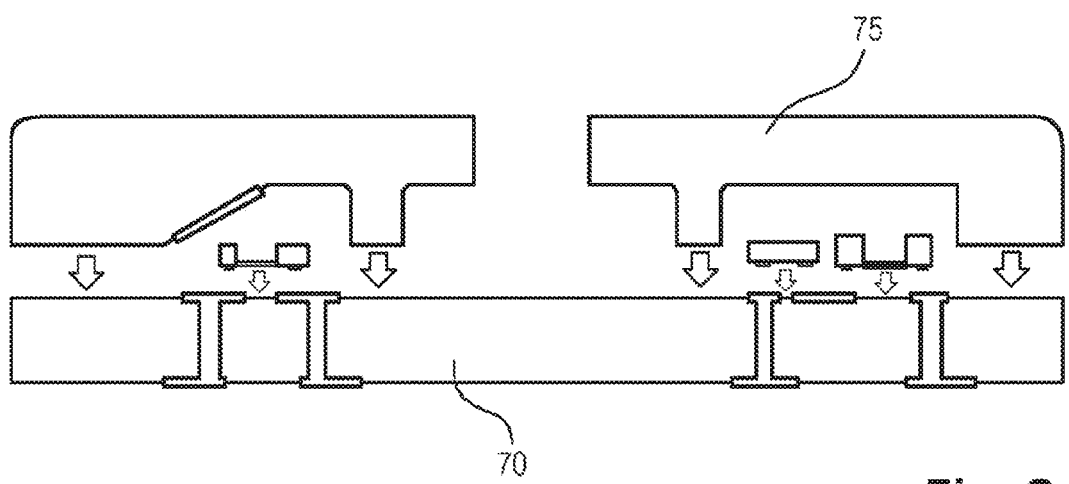
FIG. 8 shows a schematic cross sectional side view representation comparable to FIG. 7B showing the attachment of a cap member to the substrate for fabricating a photo-acoustic gas sensor according to FIG. 3.

FIG. 8 also shows a cross-sectional view along a plane indicated by line B-B indicated in FIG. 7A wherein, however, a photo-acoustic gas sensor according to the example of FIG. 3 is fabricated. In this case, after processing the semiconductor wafer 70, the light emitter units 72 and detector units 73 are attached to the upper surface of the silicon wafer 70 in a flip-chip manner and electrically connected with respective electric contact areas thereon. Thereafter, a cap member 75 is attached onto the upper surface of the silicon wafer 70 and connected thereto by anyone of the connection methods as were described before.

In a last step of the fabrication method, the multiple sensor panel is singulated into individual gas sensor units by, for example, sawing along the lines separating the regions 71 as shown in FIG. 7A.

Figure 9A:
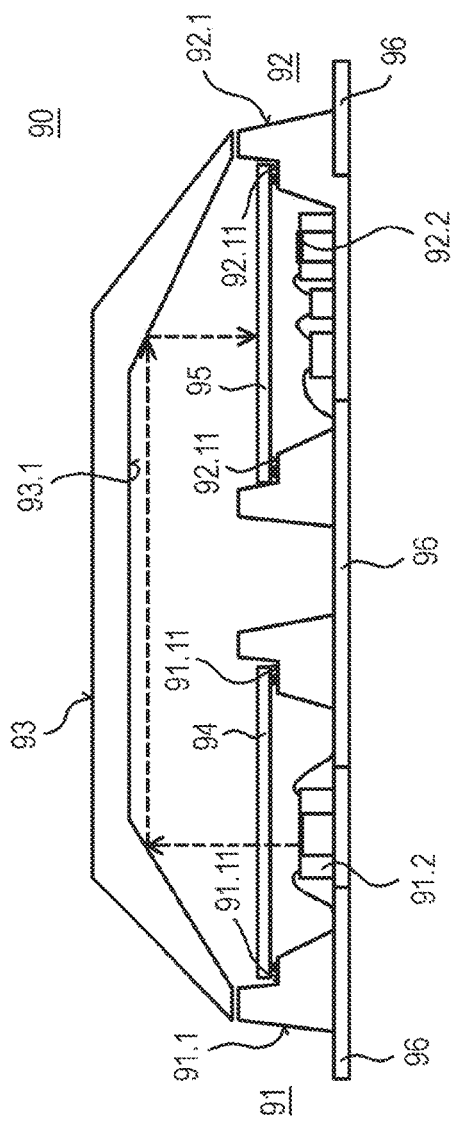
FIG. 9 includes FIGS. 9A and 9B and shows a schematic cross-sectional side view representation of a photoacoustic gas sensor wherein emitter and detector are each disposed in pre-fabricated cavities, wherein the cavities are arranged side-by-side and a cap member with an inner reflective wall is disposed above the cavities (A), and a schematic top view representation of the photoacoustic gas sensor module before mounting the cap member (B).
Figure 9B:
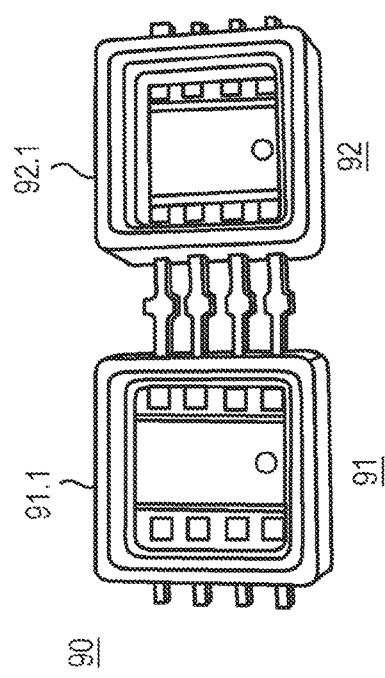

FIG. 9 includes FIGS. 9A and 9B and shows an example of a photoacoustic gas sensor according to the forth aspect. The photoacoustic gas sensor 90 as shown in FIG. 9 includes a light emitter unit 91 which includes a light emitter cavity 91.1 and a light emitter element 91.2 disposed in the light emitter cavity 91.1. The light emitter element 91.2 is configured to emit a beam of light pulses with a predetermined repetition frequency and a predetermined wavelength corresponding to an absorption band of a gas to be sensed. The light emitter element 91.2 can have any configuration or design as was described above for the light emitters of the previous examples. The photoacoustic gas sensor 90 further includes a detector unit 92 which includes a detector cavity 92.1 and a detector element 92.2 disposed in the detector cavity 92.1. The beam of light pulses traverses an area intended to accommodate the gas and the detector element 92.2 is arranged to detect a signal oscillating with the repetition frequency. The detector element 92.2 may include a microphone as in the previous examples. Further electrical devices can be disposed in the detector cavity 92.1 and connected with the detector element 92.2.

According to the example as shown in FIG. 9, the photoacoustic gas sensor 90 does not include a reference volume such as that shown in some of the previous examples.

According to the example as shown in FIG. 9, each one of the light emitter cavity 91.1 and the detector cavity 92.1 includes a bottom wall and four side walls, wherein the side walls are connected to the bottom wall and are circumferentially interconnected. According to an example thereof, the light emitter cavity 91.1 and the detector cavity 92.1 are fabricated from any sort of plastic material as, for example, any sort of resin material or mold material or any other material mentioned above in connection with encapsulant or encapsulating materials. Moreover, the light emitter cavity 91.1 and the detector cavity 92.1 may be formed of one and the same material.

According to the example as shown in FIG. 9, the light emitter cavity 91.1 and the detector cavity 92.1 are disposed laterally side-by-side so that their respective bottom walls are arranged in one and the same plane. The photoacoustic gas sensor according to the example of FIG. 9 further includes a cap member 93 being disposed above both the light emitter cavity 91.1 and the detector cavity 92.1 and being secured to the upper ends of the outer side walls of the cavities 91.1 and 91.2 by, for example, an adhesive. The gas to be sensed may flow into the interior of the device in an area between the cavities 91.1 and 91.2. The cap member 93 can be configured like any one of the cap members shown and described in the previous examples. In particular, the cap member 93 is configured to define the area intended to accommodate the gas and being configured to deflect the beam of light pulses emitted by the light emitter unit 91 in the direction of an area adjacent to the detector unit 92. According to an example thereof the cap member 93 includes an inner wall 93.1 which is highly reflective for the wavelength of the beam of light pulses by, for example, a reflective layer disposed onto the inner wall 93.1. The inner reflective wall 93.1 of the cap member 93 as shown in FIG. 9 includes two plane inclined walls, each one being disposed above one of the light emitter unit 91 and the detector unit 92 wherein the inclined walls are oriented such that the beam of light pulses is deflected as described above. The geometry of the inner wall 93.1 of the cap member 93 may also have an ellipsoidal form, wherein the light emitter element 91.2 and the detector element 92.2 may be disposed in the focal points of the ellipse. Furthermore the cap member 93 can be made of one and the same material as the light emitter cavity 91.1 and the detector cavity 92.1.

According to the example as shown in FIG. 9, the photoacoustic gas sensor 90 includes an optical filter 94 disposed before either one of the light emitter unit 91 or the detector unit 92. As was explained in connection with another example, an optical filter 94 is needed if the light emitter element 91.2 is configured in the form of a broad band light emitter element and the optical filter 94 may be configured as described in connection with one of the previous examples and, for example, such that it includes a narrow band transmission region at or around the predetermined wavelength. According to a further example thereof, the side walls of at least one of the light emitter cavity 91.1 and the detector cavity 92.1 include a circumferential inward protrusion or shoulder 91.11 in order to allow the optical filter to be fixed between the side walls in the respective cavity. The optical filter 94 can be fixed to the protrusion 91.11 by an adhesive. According to the example shown in FIG. 9, the optical filter 94 is mounted in the light emitter cavity 91.1. Furthermore according to the example shown in FIG. 9, the detector cavity 92.1 can also include a similar protrusion 92.11 for fixing an optical lid 95 thereto. The optical lid or plate 95 serves only the purpose of protecting the detector element 92.2 and can be configured in the form of a thin plate which should be at least partly transmissive for light of the predetermined wavelength. It is also possible that the optical filter 94 is mounted in the detector cavity 92.1 and the optical lid 95 is mounted in the light emitter cavity 91.1. Furthermore it is also possible that no optical filter 94 is used, but instead only optical lids 95 are mounted in the light emitter and detector cavities for protecting the light emitter element and the detector element, namely in the case that a narrow band light emitter element is used which emits only light of a narrow band around the predetermined wavelength.

According to the example as shown in FIG. 9, the photoacoustic gas sensor 90 further includes contact leads 96 which extend into the cavities 91.1 and 91.2 so that the light emitter element 91.2 and the detector element 92.2 can be connected to the inner ends of the contact leads 96 by, for example, wire bonds as shown. The contact leads 96 may be disposed in or around the same plane as the bottom walls of the cavities 91.1 and 91.2. The contact leads 96 extend to the outside so that they can be connected to a printed circuit board (PCB), for example. The contact leads 96 may be fabricated from a leadframe and the lower portion of the photoacoustic gas sensor 90 as shown in FIG. 9B may be fabricated by molding the two cavities 91.1 and 91.2 to the leadframe.

Figure 10A:
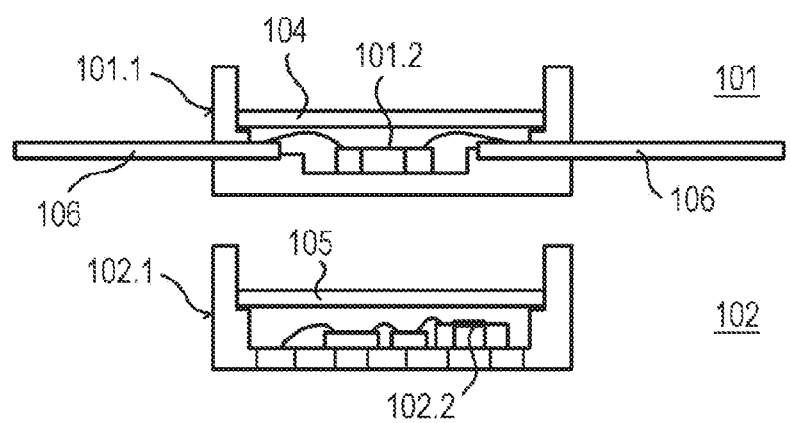
FIG. 10 includes FIG. 10A to 10C and shows a schematic cross-sectional side view representation of an emitter module and a detector module, the modules disposed in pre-fabricated cavities (A), a schematic cross-sectional side view representation of the assembled photoacoustic gas sensor module wherein the cavities are disposed in an opposite relationship (B), and a schematic down view representation of the assembled photoacoustic gas sensor module (C).
Figure 10B:
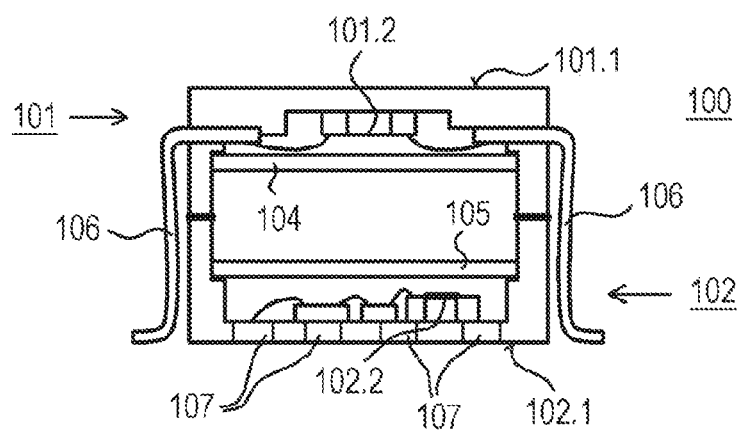
Figure 10C:
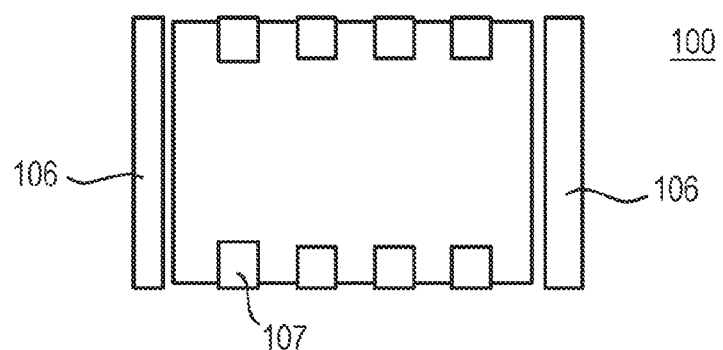

FIG. 10 includes FIG. 10A to 10C and shows an example of a photoacoustic gas sensor according to the forth aspect. The photoacoustic gas sensor 100 of FIG. 10 includes a light emitter unit 101 and a detector unit 102. The light emitter unit 101 includes a light emitter cavity 101.1 and a light emitter element 101.2 disposed in the cavity 101.1. Likewise the detector unit 102 includes a detector cavity 102.1 and a detector element 102.2 like, for example, a microphone disposed in the cavity 102.1. According to the example of FIG. 10 and as can be seen in FIG. 10B, the light emitter cavity 101.1 and the detector cavity 102.1 are disposed in an opposite relationship so that their respective side walls are connected with each other by, for example, an adhesive, and the light emitter unit 101 and the detector unit 102 are facing each other. An opening will be provided in at least one sidewall of one or both of the cavities 101.1 and 102.1 for the gas to flow into the interior of the sensor. The photoacoustic gas sensor 100 may further include an optical filter 104 and an optical lid 105 which can have the same functions as the respective elements of the previous example. The photoacoustic gas sensor 100 may further include two first contact leads 106 which are both connected with the light emitter unit 101 and are bent downwards to the plane of the bottom plate of the detector cavity 102.1. Second contact leads 107 are provided in the detector cavity 102.1, wherein the second contact leads 107 extend through the bottom plate of the detector cavity 102.1 so that the detector element 102.2 and possible further electrical devices can be electrically connected to the second contact leads 107 by, for example, either back surface electrical contact pads or bond wires.

FIG. 10A indicates a possible method of fabricating the photoacoustic gas sensor 100. The light emitter unit 101 and the detector unit 102 are fabricated independently whereas the emitter unit can be fabricating by molding around the two first contact leads 106 and the detector unit can be fabricated by molding around the second contact leads 107. Thereafter the emitter element 101.2 is disposed in the cavity 101.1 and electrically connected to the inner ends of the first contact leads 106 by, for example, wire bonds. Likewise the detector element 102.2 and possibly further electrical devices are disposed in the detector cavity 102.1 and electrically connected to the second contact leads 107 by, for example, soldering or wire bonds. Thereafter the emitter unit 101 is placed onto the detector unit 102 by adhering the respective side walls to each other and then the first contact leads 106 are bent down to the plane of the bottom wall of the detector cavity 102.1.

Figure 11A:
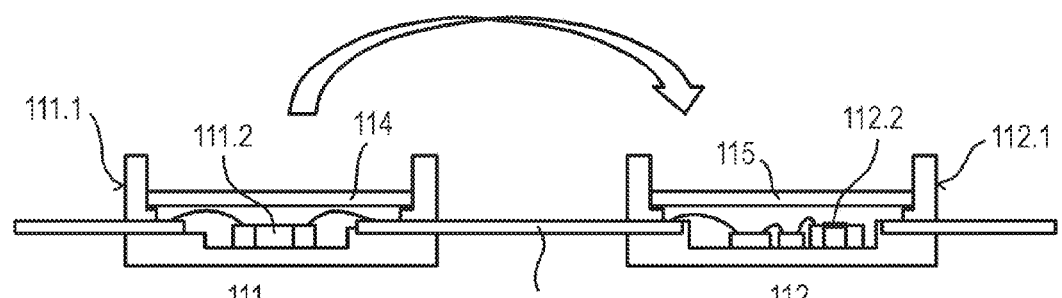
FIG. 11 includes FIG. 11A to 11C and shows a schematic cross-sectional side view representation of an emitter module and a detector module, the modules disposed in pre-fabricated cavities and the modules being electrically connected with each other (A), a schematic cross-sectional side view representation of the assembled photoacoustic gas sensor module wherein the cavities are disposed in an opposite relationship (B), and a schematic down view representation of the assembled photoacoustic gas sensor module (C).
Figure 11B:
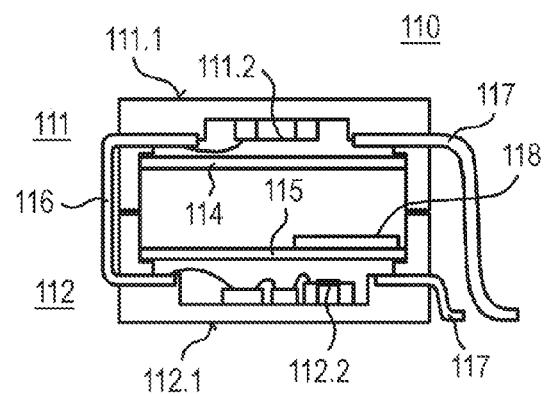
Figure 11C:
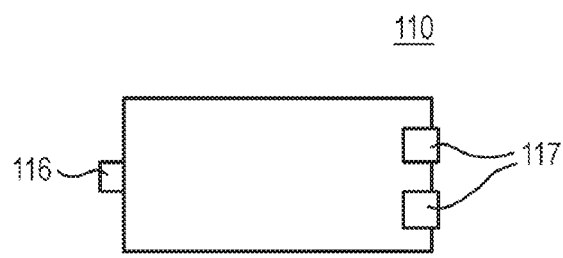

FIG. 11 includes FIG. 11A to 11C and shows an example of a photoacoustic gas sensor according to the forth aspect. The photoacoustic gas sensor 110 as shown in FIG. 11B corresponds in principle to the photoacoustic gas sensor 100 of the previous example in FIG. 10 in so far as the light emitter unit 111 and the detector unit 112 are disposed in an opposite relationship so that their respective side walls are connected with each other by, for example, an adhesive, and the light emitter unit 111 and the detector unit 112 are facing each other. A difference to the sensor of FIG. 10 is the way of electrically connecting the light emitter unit 111 and the detector unit 112 to each other and to the outside. In the example of FIG. 11 a first contact lead 116 is provided which connects the light emitter unit 111 to the detector unit 112. Furthermore second contact leads 117 are provided which are connected to either one of the emitter unit 111 and the detector unit 112 and are both bent down to the plane of the bottom wall of the detector unit 112. FIG. 11A further indicates a possible way of fabricating the photoacoustic gas sensor 110, namely by first fabricating an intermediate product as shown in FIG. 11A in which both the light emitter unit 111 and the detector unit 112 are fabricated and electrically to each other by the first contact lead 116 and afterwards bending the light emitter unit 111 as indicated by the arrow towards the detector unit 112 and then fixing the respective side wall to each other by, for example, an adhesive. The elements designated with the reference signs 111.1 (light emitter cavity), 111.2 (light emitter element), 112.1 (detector cavity), 112.2 (detector element), 114 (optical filter), and 115 (optical lid) are similar to those of the previous examples of a photoacoustic gas sensor. The detector unit 112 may further include an light absorber layer 118 in case that a direct irradiation of the detector element 112.2 shall be avoided.

Figure 12A:
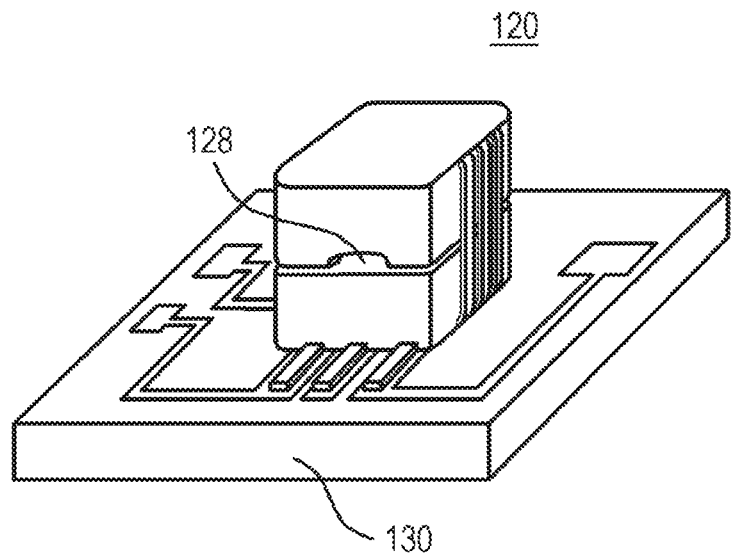
FIG. 12 includes FIGS. 12A and 12B and shows a perspective view representation of an emitter module and detector module, the modules being electrically connected to each other (A), and a perspective view representation of the assembled photoacoustic gas sensor module mounted on a printed circuit board (PCB).
Figure 12B:
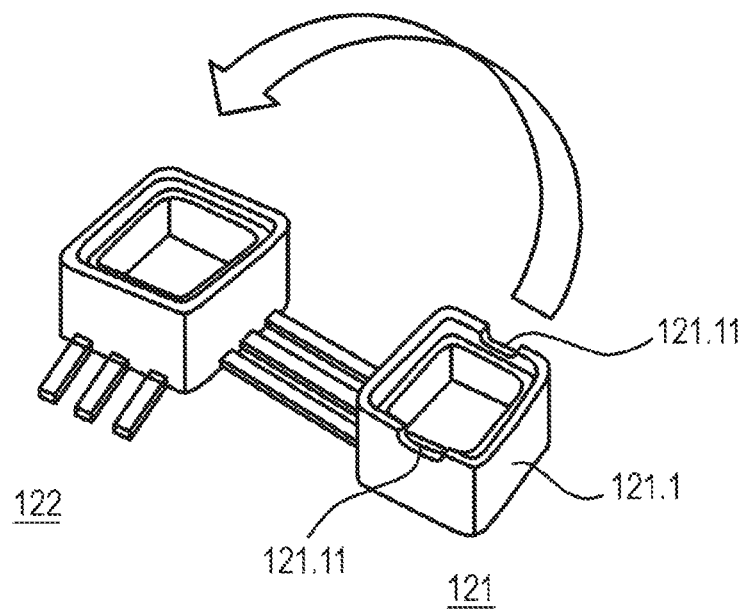

FIG. 12 includes FIGS. 12A and 12B and shows an example of a photoacoustic gas sensor according to the forth aspect. The photoacoustic gas sensor 120 of FIG. 12A and its fabrication method as indicated in FIG. 12B are similar to those of the previous example of FIG. 11 so that the details will not be repeated here. The example of FIG. 12 shows as a further feature how a gas inlet opening can be provided. As shown in FIG. 12B, a recess 121.11 can be formed in one or more side walls of the light emitter cavity 121.1 of the light emitter unit 121. When assembling the photoacoustic sensor device 120 as shown by the arrow in FIG. 12B, the recesses 121.11 result in a gas inlet opening 128 as shown in FIG. 12A. FIG. 12A also shows the photoacoustic sensor device 120 mounted on and electrically connected to a printed circuit board (PCB) 130.

The present disclosure also relates to a method for fabricating a photo-acoustic gas sensor according to a fifth aspect, wherein the method includes providing a light emitter unit including a light emitter cavity and a light emitter element disposed in the light emitter cavity, the light emitter element being configured to emit a beam of light pulses with a predetermined repetition frequency and a predetermined wavelength corresponding to an absorption band of a gas to be sensed, and providing a detector unit including a detector cavity and a detector element disposed in the detector cavity, wherein the beam of light pulses traverses an area intended to accommodate the gas and the detector element is arranged to detect a signal oscillating with the repetition frequency.

According to an example of the method of the fifth aspect, the method includes fabricating a photoacoustic gas sensor according to the forth aspect and, in particular, a photoacoustic gas sensor as described above in connection with one of FIGS. 9 to 12.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A photo-acoustic gas sensor, comprising:
   a substrate;
   electronic circuitry integrated in the substrate;
   a light emitter unit supported by the substrate, the light emitter unit comprising a light emitter controlled by the electronic circuitry and configured to emit a beam of light pulses with a predetermined repetition frequency and wavelength corresponding to an absorption band of a gas to be sensed;
   a detector unit supported by the substrate, the detector unit comprising a microphone; and
   a cap member disposed above the substrate and configured to define an area intended to accommodate the gas, wherein the cap member is comprised of one or more of a semiconductor material, a silicon-based material, a glass material, and a ceramic material,
   wherein the beam of light pulses traverses the area intended to accommodate the gas, and wherein the microphone is configured to receive a signal oscillating with the repetition frequency.

2. The photo-acoustic gas sensor according to claim 1, wherein
   the substrate comprises one or more of a semiconductor substrate, a silicon-based substrate, a glass substrate, and a ceramic substrate.

3. The photo-acoustic gas sensor according to claim 1, wherein
   the substrate comprises a silicon-based semiconductor substrate, and
   one or more of the light emitter and the microphone is integrated in the semiconductor substrate.

4. The photo-acoustic gas sensor according to claim 1, wherein
   the substrate comprises a silicon-based semiconductor substrate, and
   one or more of the light emitter and the microphone is at least in part contiguous with the semiconductor substrate.

5. The photo-acoustic gas sensor according to claim 1, wherein
   one or more of the light emitter unit and the detector unit is comprised of a prefabricated module attached to the substrate.

6. The photo-acoustic gas sensor according to claim 1, further comprising:
   a reference gas; and
   the detector unit comprising a detector unit chamber;
   wherein the substrate and the cap member are further configured to define the detector unit chamber and the reference gas is enclosed in the detector unit chamber, wherein the reference gas is of the same species as the gas to be sensed.

7. The photo-acoustic gas sensor according to claim 1, further comprising:
   the light emitter unit comprising a light emitter unit chamber;
   wherein the substrate and the cap member are further configured to define the light emitter unit chamber.

8. The photo-acoustic gas sensor according to claim 1, wherein
   the cap member is configured to deflect the beam of light pulses emitted by the light emitter unit in the direction of an area adjacent to the detector unit.

9. The photo-acoustic gas sensor according to claim 1, wherein
the cap member comprises an opening between the environment and the area intended to accommodate the gas.

10. The photo-acoustic gas sensor according to claim 1, further comprising:
a bottom member disposed below the substrate, wherein the bottom member is comprised of one or more of a semiconductor material, a silicon-based material, a glass material, and a ceramic material.

11. A photo-acoustic gas sensor module, comprising:
a substrate;
electronic circuitry integrated in the substrate;
a light emitter controlled by the electronic circuitry and configured to emit a beam of light pulses to be absorbed by a gas;
a detector configured to receive a signal oscillating with a repetition frequency of the light pulses; and
a cap member disposed above the substrate and configured to define an area intended to accommodate the gas, wherein the cap member is comprised of one or more of a semiconductor material, a silicon-based material, a glass material, and a ceramic material, and
wherein the light emitter and the detector are supported by the substrate.

12. The photo-acoustic gas sensor according to claim 11, wherein
the substrate comprises electrical via connections connected with the light emitter and the detector.

13. The photo-acoustic gas sensor according to claim 11, wherein
the cap member comprises a reflective wall configured to reflect the beam of light pulses emitted by the light emitter in the direction of an area adjacent to the detector.

14. The photo-acoustic gas sensor according to claim 11, further comprising:
a bottom member disposed below the substrate, the bottom member comprising electrical via connections.

15. A photoacoustic gas sensor, comprising:
a light emitter unit comprising a light emitter cavity and a light emitter element disposed in the light emitter cavity, the light emitter element being configured to emit a beam of light pulses with a predetermined repetition frequency and a predetermined wavelength corresponding to an absorption band of a gas to be sensed;
a detector unit comprising a detector cavity and a detector element disposed in the detector cavity; and
contact leads which extend between the light emitter cavity and the detector cavity, each contact lead having ends that extend inside of the light emitter cavity and the detector cavity,
wherein the beam of light pulses traverses an area intended to accommodate the gas and the detector element is arranged to detect a signal oscillating with the repetition frequency.

16. The photoacoustic gas sensor according to claim 15 wherein
each one of the light emitter cavity and the detector cavity comprises a bottom wall and four side walls, wherein the side walls are connected to the bottom wall and are circumferentially interconnected.

17. The photoacoustic gas sensor according to claim 16, further comprising:
a cap member being disposed above both the light emitter cavity and the detector cavity and being configured to define the area intended to accommodate the gas and being configured to deflect the beam of light pulses emitted by the light emitter unit in the direction of an area adjacent to the detector unit; wherein
the light emitter cavity and the detector cavity are disposed laterally side-by-side so that their respective bottom walls are arranged in one and the same plane.

18. The photoacoustic gas sensor according to claim 15, wherein
the light emitter cavity and the detector cavity are disposed in an opposite relationship so that their respective side walls are connected with each other and the light emitter unit and the detector unit are facing each other.

19. The photoacoustic gas sensor according to claim 15, further comprising:
an optical filter disposed before either one of the light emitter unit or the detector unit.

20. A method for fabricating the photo-acoustic gas sensor of claim 1, comprising
providing a substrate;
fabricating a multiple sensor panel by forming a plurality of gas sensor units, each one of the plurality of gas sensor units being supported by the substrate and comprising a light emitter unit and a detector unit; and
singulating the multiple sensor panel to obtain a plurality of photo-acoustic gas sensors.

21. The method according to claim 20, wherein
forming the plurality of gas sensor units comprises integrating the light emitter unit and the detector unit into an area adjacent to an upper main face of the substrate.

22. The method according to claim 20, wherein
forming the plurality of gas sensor unit comprises prefabricating a light emitter unit and a detector unit and disposing the light emitter unit and the detector unit above an upper main face of the substrate.

* * * * *